(12) United States Patent
Chun et al.

(10) Patent No.: US 9,207,226 B2
(45) Date of Patent: Dec. 8, 2015

(54) APPARATUS AND METHOD FOR ANALYZING DRILLED SUBMARINE SEDIMENT ON SHIP

(71) Applicant: Korea Institute of Geoscience and Mineral Resources, Daejeon (KR)

(72) Inventors: Jong Hwa Chun, Daejeon (KR); Jang Jun Bahk, Daejeon (KR); Byong Jae Ryu, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 230 days.

(21) Appl. No.: 13/670,950

(22) Filed: Nov. 7, 2012

(65) Prior Publication Data

US 2013/0298661 A1   Nov. 14, 2013

(30) Foreign Application Priority Data

Nov. 9, 2011   (KR) .................. 10-2011-0116225

(51) Int. Cl.
  *E21B 49/02* (2006.01)
  *G01N 33/24* (2006.01)
(52) U.S. Cl.
  CPC .................... *G01N 33/241* (2013.01)
(58) Field of Classification Search
  CPC ...................... E21B 49/005; G01N 33/241
  USPC ................. 73/152.09, 152.011, 152.07
  See application file for complete search history.

(56) References Cited

U.S. PATENT DOCUMENTS

| | | | | |
|---|---|---|---|---|
| 3,670,830 A | * | 6/1972 | Van Der Wijden | 175/52 |
| 4,790,180 A | * | 12/1988 | Sinnokrot | 73/152.07 |
| 5,388,456 A | * | 2/1995 | Kettel | 73/152.02 |
| 5,741,959 A | * | 4/1998 | Garcia et al. | 73/19.05 |
| 8,131,468 B2 | * | 3/2012 | Kischkat et al. | 702/6 |
| 8,191,436 B2 | | 6/2012 | Chun et al. | |
| 2006/0287201 A1 | * | 12/2006 | Georgi et al. | 507/100 |
| 2009/0321132 A1 | * | 12/2009 | Ouellet et al. | 175/11 |
| 2010/0223989 A1 | * | 9/2010 | Reid et al. | 73/152.11 |

(Continued)

FOREIGN PATENT DOCUMENTS

| | | |
|---|---|---|
| JP | 1209896 A | 8/1989 |
| JP | 200971346 A | 4/2009 |

(Continued)

OTHER PUBLICATIONS

Lee, Young-Joo, "Gas Hydrate Exploration by using PCS(Pressre Core Sampler): ODP Leg 204", Econ. Environ. Geol., 2005, pp. 165-176, vol. 38(2), Petroleum and Marine Resource Division, KIGAM, Daejon 305-350, Korea.

(Continued)

*Primary Examiner* — Eric S McCall
*Assistant Examiner* — Anthony W Megna Fuentes
(74) *Attorney, Agent, or Firm* — The Webb Law Firm

(57) ABSTRACT

Provided are an apparatus and a method for analyzing drilled submarine sediment on a ship. The apparatus includes: a core temperature measuring unit measuring temperatures of each portion of the drilled core positioned on a ship; a gas content analyzing unit analyzing a kind and a content of gases included in a submarine sediment sample collected from the drilled core in a state in which it is positioned on the ship; and a salinity measuring unit measuring salinity of the submarine sediment sample collected from the drilled core in a state in which it is positioned on the ship.

5 Claims, 1 Drawing Sheet

(56) References Cited

U.S. PATENT DOCUMENTS

2010/0315081 A1* 12/2010 Chanpura et al. ............. 324/303
2011/0261987 A1 10/2011 Nakanishi et al.
2012/0204781 A1* 8/2012 Chun et al. .................... 114/312

FOREIGN PATENT DOCUMENTS

KR 100978143 B1 8/2010
KR 101048528 B1 7/2011

OTHER PUBLICATIONS

Gungho, "[Home World] Burning Sea ice drilling the second of next month . . . How", Asia Economy yigyeongho News, Jun. 29, 2010, news article, Asia Economy Broadcast.

* cited by examiner

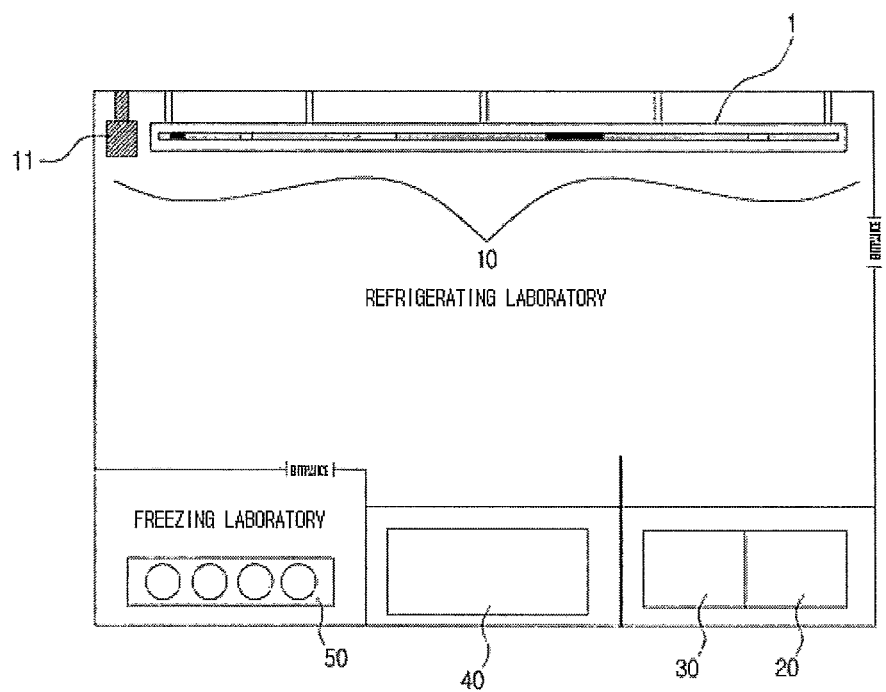

APPARATUS AND METHOD FOR ANALYZING DRILLED SUBMARINE SEDIMENT ON SHIP

CROSS-REFERENCE TO RELATED APPLICATIONS

This application claims priority under 35 U.S.C. §119 to Korean Patent Application No. 10-2011-0116225, filed on Nov. 9, 2011, in the Korean Intellectual Property Office, the disclosure of which is incorporated herein by reference in its entirety.

TECHNICAL FIELD

The following disclosure relates to an apparatus and a method for analyzing a collected sample secured through ocean exploration for examining whether or not gas hydrate is present.

BACKGROUND

Ocean exploration has been conducted in order to search resources present on the seabed, such as petroleum, natural gas, gas hydrate, and the like.

Generally, in an ocean exploration method, exploration of predicting whether or not submarine resources such as petroleum, natural gas, gas hydrate, and the like, are present using a seismic exploration method, an unmanned underwater vehicle, or the like, is preferentially performed.

The seismic exploration method is a method based on a feature that an interval velocity of a seismic wave in pure gas hydrate is faster than that of a seismic wave in a sedimentary layer, such that an interval velocity of the seismic wave in a sedimentary layer containing gas hydrate is faster than that of the seismic wave in a sedimentary layer not containing gas hydrate and a feature that a seismic chimney, or the like, is shown in a cross-sectional view of the seismic wave and gas hydrate, or the like, is present at an upper portion of the seismic chimney.

The exploration method using the unmanned underwater vehicle is a method for exploring whether or not the gas hydrate is present by measuring concentrations of methane gas through injection of an exploration apparatus into the seabed since the methane gas is discharged in the case in which the gas hydrate is present on the seabed.

Korean Patent No. 10-1048528 has suggested an exploration method using an unmanned underwater vehicle.

When it is determined by the seismic exploration method and the exploration method using an unmanned underwater vehicle as described above that the submarine resource such as gas hydrate, or the like is present, a drilling apparatus descends to a submarine surface of a corresponding point to perform drilling, thereby directly confirming whether or not the submarine resource is present.

Korean Patent No. 10-0978143 has suggested a structure of an apparatus for drilling submarine sediment.

Meanwhile, the gas hydrate, which is a new clean energy source of the 21 century capable of substituting fossil fuels and an energy source formed by being combined with water in a low temperature and high pressure state of the permafrost or the deep sea, has an appearance similar to that of dry ice and has a property that it may be burned with fire, such that it is also called burning ice (a main component of the gas hydrate is methane gas).

However, since most of the gas hydrate is positioned at the deep sea, a significantly long time is required to obtain drilled gas hydrate in a state in which it is filled in a core in gas hydrate exploration onto a ship. In addition, when the gas hydrate is obtained onto the ship in a state in which it is changed in a low temperature and high pressure environment to a room temperature and normal pressure environment, the gas hydrate is in a state in which it is significantly dissociated or completely dissociated.

According to the related art, after the gas hydrate drilled in a state in which it is filled in the core is put in liquid nitrogen and moved to a laboratory on land, an analysis experiment for examining whether or not the gas hydrate is present has been conducted.

Therefore, an original form or component is contaminated during a process of moving the gas hydrate obtained onto the ship to the laboratory on land, such that it is difficult to secure accuracy of the analysis experiment (the gas hydrate is completely dissociated generally in one hour).

As a result, reliability of judgment of whether or not the gas hydrate is present has been decreased.

RELATED ART DOCUMENT

Patent Document (Patent Document 1) Korea Patent No. 10-1048528
(Patent Document 2) Korea Patent No. 10-0978143

SUMMARY

An embodiment of the present invention is directed to providing an apparatus and a method for analyzing a collected sample on a ship capable of increasing reliability of an analysis experiment by allowing an analysis experiment for examining whether or not gas hydrate is present to be rapidly performed when submarine sediment collected through a submarine sediment drilling apparatus is obtained onto the ship.

In an exemplary embodiment of the present invention, temperatures of each portion of a drilled core obtained onto a ship are measured to confirm a portion where it is doubted whether gas hydrate is present and allow a gas content and salinity of submarine sediment collected by cutting the portion where it is doubted whether the gas hydrate is present to be analyzed on the ship, thereby making it possible to improve reliability of an analysis experiment of the collected submarine sediment.

An apparatus according to the exemplary embodiment of the present invention is to analyze submarine sediment drilled in a form in which it is filled in a drilled core through ocean exploration.

In addition, the apparatus according to the exemplary embodiment of the present invention includes a core temperature measuring unit measuring temperatures of each portion of the drilled core positioned on a ship.

Further, the apparatus according to the exemplary embodiment of the present invention includes a gas content analyzing unit analyzing a kind and a content of gases included in a submarine sediment sample collected from the drilled core in a state in which it is positioned on the ship.

In addition, the apparatus according to the exemplary embodiment of the present invention includes a salinity measuring unit measuring salinity of the submarine sediment sample collected from the drilled core in a state in which it is positioned on the ship.

A method according to the exemplary embodiment of the present invention is to analyze submarine sediment drilled in a form in which it is filled in a drilled core through ocean exploration.

In addition, the method according to the exemplary embodiment of the present invention includes an estimated portion search step of detecting temperatures of each portion of the drilled core and then obtained to thereby be positioned on the ship to search a portion where it is doubted that gas hydrate is present and a portion where it is not doubted that the gas hydrate is present.

Further, the method according to the exemplary embodiment of the present invention includes a gas content analyzing step of analyzing a kind and a content of gases included in a submarine sediment sample collected from the drilled core on the ship on the ocean after the estimated portion search step.

Further, the method for analyzing submarine sediment includes a salinity measuring step of measuring salinity of the submarine sediment sample collected from the drilled core on the ship after the estimated portion search step.

BRIEF DESCRIPTION OF THE DRAWINGS

FIG. 1 is a schematic view for describing a structure in which components such as a core temperature measuring unit, a gas content analyzing unit, a salinity measuring unit, a particle size analyzer, and the like, are positioned in a refrigerating laboratory provided on a ship and a freezing storage unit is positioned in a freezing laboratory provided on the ship.

DETAILED DESCRIPTION OF MAIN ELEMENTS

1: Drilled core
10: Core temperature measuring unit
11: Infrared camera
20: Gas content analyzing unit
30: Salinity measuring unit
40: Particle size analyzer
50: Freezing storage unit Detailed Description of Embodiments Hereinafter, a technical spirit of the present invention will be described in more detail with reference to the accompanying drawings.

However, the accompanying drawings are only examples shown in order to describe the technical idea of the present invention in more detail. Therefore, the technical idea of the present invention is not limited to shapes of the accompanying drawings.

The present invention relates to an apparatus for analyzing submarine sediment drilled in a form in which it is filled in a drilled core through ocean exploration.

An object of the present invention is to provide an apparatus and a method capable of increasing of analysis experiment for examining whether or not gas hydrate is present.

To this end, the present invention suggests an apparatus and a method for rapidly analyzing submarine sediment collected through a submarine sediment drilling apparatus on a ship when the submarine sediment is obtained onto the ship (a drilled core is positioned in a pipe type barrel (external pipe), such that submarine sediment is filled in the drilled core during a drilling process. A method of collecting a sample for analysis from this drilled core has been well-known).

Even though the submarine sediment in the drilled core is analyzed on the ship, when a long time elapses, the analysis is meaningless.

Therefore, it is very important to rapidly search a portion where it is doubted whether gas hydrate is present and collect a sample for analysis therefrom.

To this end, the apparatus for analyzing submarine sediment according to an exemplary embodiment of the present invention includes a core temperature measuring unit 10 capable of measuring temperatures of each portion of the drilled core 1 positioned on the ship.

Since the gas hydrate has an ice crystal form similar to dry ice, even though the gas hydrate is dissociated while being melted when it is obtained in a state in which it is present in the drilled core 1, a portion at which the gas hydrate is present has a temperature relatively lower than that of a portion at which the gas hydrate is not present. Therefore, temperatures of each point of the drilled core are measured, thereby making it possible to search a portion where it is doubted that the gas hydrate is present or has been present.

In the above description, the temperature measurement may be temperature measurement at an accurate numerical value or measurement for examining whether a specific portion has a temperature significantly lower than the surrounding through an infrared camera 11.

That is, since it is sufficient for the core temperature measuring unit 10 according to the exemplary embodiment of the present invention to search a portion where it is doubted that the gas hydrate is present and a portion where it is not doubted that the gas hydrate is present, it is sufficient that the core temperature measuring unit 10 according to an exemplary embodiment of the present invention includes the infrared camera 11, or the like.

When the infrared camera 11 photographs the drilled core 1 while moving in a length direction of the drilled core 1, thereby schematically measuring (displaying) a temperature, the portion where it is doubted that the gas hydrate is present and the portion where it is not doubted that the gas hydrate is present may be rapidly found out.

Even though the portion where it is doubted that the gas hydrate is present and the portion where it is not doubted that the gas hydrate is present are found out and a sediment sample (a sample for an analysis experiment) of the corresponding portions are collected, it is important what analysis is performed on the corresponding sample to examine whether the gas hydrate is present.

The apparatus for analyzing submarine sediment according to the exemplary embodiment of the present invention includes a gas content analyzing unit 20 analyzing a kind and a content of gases (methane gas, ethane gas, propane gas, and the like) in a submarine sediment sample collected from the drilled core 1 in a state in which it is positioned on the ship.

In addition, the apparatus for analyzing submarine sediment according to the exemplary embodiment of the present invention includes a salinity measuring unit 30 measuring salinity of the submarine sediment sample collected from the drilled core 1 in a state in which it is positioned on the ship.

That is, when the methane gas, the ethane gas, the propane gas, and the like, are present in the collected sample and amounts of them are larger than amounts of methane, ethane, propane, and the like, present in samples collected at other points in the drilled core, it may be considered as one element capable of being guessed as a phenomenon generated due to melting of gas hydrate.

In addition, when salinity of the collected sample is lower than that of samples collected at other points in the drilled core, it may be guessed that the gas hydrate in the ice crystal form is melted to increase a ratio of fresh water, such the salinity is decreased.

Since the gas hydrate is generally a crystal of gas, particularly, methane gas and water, when the gas hydrate is melted, a large amount of gas and water (fresh water) are generated.

Further, when a content of propane gas exceeds 10%, it may be judged that the gas hydrate is a thermogenic source.

Since the gas content analyzing unit 20 or the salinity measuring unit 30 as described above is not significantly affected by shaking, even though it is driven in a state in which it is positioned on a ship on the ocean, a problem is not generated in reliability of analysis.

Further, since economic efficiency of mining after exploration may be judged according to what gas configures the gas hydrate, it is very effective for the apparatus for analyzing submarine sediment according to the exemplary embodiment of the present invention to include the gas content analyzing unit 20.

A method for analyzing submarine sediment using the apparatus for analyzing submarine sediment according to the exemplary embodiment of the present invention as described above includes an estimated portion search step of detecting temperatures of each portion of the drilled core 1 drilled and then lifted to thereby be positioned on the ship to search a portion where it is doubted that gas hydrate is present and a portion where it is not doubted that the gas hydrate is present.

In addition, the method for analyzing submarine sediment includes a gas content analyzing step of analyzing a content of methane gas, ethane gas, and propane gas in a submarine sediment sample collected from the drilled core 1 on a ship on the ocean after the estimated portion search step.

Further, the method for analyzing submarine sediment includes a salinity measuring step of measuring salinity of the submarine sediment sample collected from the drilled core 1 on the ship after the estimated portion search step.

The estimated portion search step, the gas content analyzing step, and the salinity measuring step as described above are performed in order to examine whether or not the gas hydrate has been present in the drilled core 1.

In the apparatus for analyzing submarine sediment according to the exemplary embodiment of the present invention, since it is very important in judging economic efficiency of mining to examine a state of a stratum at the portion where it is doubted that the gas hydrate is present, it is very important to examine the state of the stratum at the portion where it is doubted that the gas hydrate is present.

That is, payability of mining is better in the case in which the gas hydrate is present in a sand sediment as compared with in the case in which the gas hydrate is present in a mud sediment.

The apparatus for analyzing submarine sediment according to the exemplary embodiment of the present invention may further include a particle size analyzer 40 in order to recognize the state of the stratum at the portion where it is considered that the gas hydrate is present.

That is, when the apparatus for analyzing submarine sediment according to the exemplary embodiment of the present invention may further include the particle size analyzer 40 analyzing a particle size of the submarine sediment sample collected from the drilled core 1 in a state in which it is positioned on the ship to further perform a particle size analyzing step, it may be recognized whether the sediment at the portion where it is considered that the gas hydrate is present is the mud stratum, the sand stratum, or other stratum.

The apparatus for analyzing submarine sediment according to the exemplary embodiment of the present invention may be implemented to further include a freezing storage unit 50 freezing and storing a cut drilled core 1 when the cut drilled core 1 is injected thereinto in a state in which it is positioned on the ship.

When the freezing storage unit is provided on the ship to freeze and store a sample together with data on a point at which the sample has been collected, or the like, since an analysis result on the ship may be subsequently verified in a precise analytical laboratory on land, or the like, reliability of analysis may be raised.

The more rapid the freezing speed, the better the freezing storage unit 50.

Therefore, it is more preferable that the apparatus for analyzing submarine sediment according to the exemplary embodiment of the present invention includes the freezing storage unit 50 configured to rapidly freeze the drilled core 1 using liquid nitrogen.

The gas content analyzing unit, the salinity measuring unit, the particle size analyzer, and the freezing storage unit, which are components of the apparatus for analyzing submarine sediment according to the exemplary embodiment of the present invention, may be implemented to have the same structure as a structure that has been widely used in various industrial fields.

In addition, it is preferable that the core temperature measuring unit, the gas content analyzing unit, the salinity measuring unit, the particle size analyzer, and the freezing storage unit, and the like, which are components of the apparatus for analyzing submarine sediment according to the exemplary embodiment of the present invention are positioned in a refrigerating laboratory (preferably maintained at a temperature of 0 to 5° C.) provided on the ship.

It is more preferable that the freezing storage unit is positioned in a freezing laboratory provided on the ship as shown in FIG. 1.

The apparatus for analyzing submarine sediment according to the exemplary embodiment of the present invention rapidly measures the temperatures of each portion of the drilled core obtained onto the ship on the ship to search a portion where it is doubted that the gas hydrate is present and allow a gas content and salinity of submarine sediment collected by cutting the portion where it is doubted that the gas hydrate is present to be analyzed on the ship, thereby making it possible to improve reliability of a result of an experiment for examining whether or not the gas hydrate is present and characteristics of the gas hydrate.

In addition, in the case in which the apparatus for analyzing submarine sediment includes the particle size analyzer analyzing the particle size of the submarine sediment in the cut drilled core in a state in which it is positioned on the ship, since it may be detected at what sediment the gas hydrate is present, economic efficiency may also be judged.

Further, in the case in which the apparatus for analyzing submarine sediment includes the freezing storage unit freezing and storing the cut drilled core when the cut drilled core is injected thereinto, since analysis data may be subsequently verified, reliability may be further increased.

What is claimed is:

1. An apparatus for analyzing submarine sediment drilled in a form in which it is filled in a drilled core through ocean exploration, where the drilled core is placed on a ship, the apparatus comprising:
   a core temperature measuring unit measuring a temperature of a predetermined portion of the drilled core positioned on a ship to search a portion where it is doubted that gas hydrate is present and a portion where it is not doubted that gas hydrate is present;

a gas content analyzing unit analyzing a kind and a content of gases included in a sample collected from the drilled core in a state in which it is positioned on the ship; and a salinity measuring unit measuring salinity of the sample collected from the drilled core in a state in which it is positioned on the ship, wherein the core temperature measuring unit includes an infrared camera for photographing the drilled core to measure and display a relative temperature in the drilled core, and wherein the gas content analyzing unit analyzes a kind and a content of gases included in a sample collected at a portion having a relatively lower temperature among samples collected in the drilled core.

2. The apparatus of claim 1, further comprising a particle size analyzer analyzing a particle size of the sample collected from the drilled core in a state in which it is positioned on the ship.

3. The apparatus of claim 1, further comprising a freezing storage unit freezing and storing a cut drilled core when the cut drilled core is injected thereinto in a state in which it is positioned on the ship.

4. The apparatus of claim 3, wherein the freezing storage unit is configured to freeze the drilled core using liquid nitrogen.

5. The apparatus of claim 1, wherein the core temperature measuring unit includes the infrared camera photographing the drilled core while moving in a length direction of the drilled core.

* * * * *